(12) United States Patent
Jones et al.

(10) Patent No.: US 8,785,203 B2
(45) Date of Patent: Jul. 22, 2014

(54) PROTEIN DETECTION REAGENTS AND METHODS WITH DYES AND DEXTRINS

(75) Inventors: Daniel Brian Jones, Cambridge (GB); Heikki Lanckriet, Cambridge (GB)

(73) Assignee: Expedeon Limited (GB)

( * ) Notice: Subject to any disclaimer, the term of this patent is extended or adjusted under 35 U.S.C. 154(b) by 0 days.

(21) Appl. No.: 13/278,699

(22) Filed: Oct. 21, 2011

(65) Prior Publication Data

US 2012/0190120 A1     Jul. 26, 2012

Related U.S. Application Data

(62) Division of application No. 12/226,797, filed as application No. PCT/GB2007/050226 on Apr. 30, 2007.

(30) Foreign Application Priority Data

Apr. 28, 2006 (GB) .................................. 0608377.8

(51) Int. Cl.
    *G01N 33/68*      (2006.01)

(52) U.S. Cl.
    USPC .............................. 436/86; 436/164; 436/175

(58) Field of Classification Search
    CPC ....................... G01N 33/6827; G01N 33/6839
    See application file for complete search history.

(56) References Cited

U.S. PATENT DOCUMENTS

| | | | |
|---|---|---|---|
| 3,884,637 A | 5/1975 | Gindler | |
| 4,023,933 A | 5/1977 | Bradford et al. | |
| 4,239,495 A | 12/1980 | Gindler et al. | |

FOREIGN PATENT DOCUMENTS

| | | |
|---|---|---|
| JP | 2000-0321276 | 11/2000 |
| JP | 2005055417 A | 3/2005 |
| JP | 2007240337 A | 9/2007 |
| JP | 4391171 B2 | 12/2009 |

OTHER PUBLICATIONS

Couthon, Fabienne et al. "Refolding of SDS- and thermally denatured MM-creatine kinase using cyclodextrins." Biochemical and Biophysical Research Communications (1996) 227 854-860.*
Zor, Tsaffrir et al. "Linearization of the Bradford protein assay increases its sensitivity: theoretical and experimental studies." Analytical Biochemistry (1996) 236 302-308.*
Bradford, M.M. "A rapid and sensitive method for the quantitation of microgram quantities of protein utilizing the principle of protein-dye binding," *Anal. Biochem.* May 1976; 72:248-54.
Dulley, J.R. et al., "A simple technique for eliminating interference by detergents in the Lowry method of protein determination," *Anal. Biochem.* 1975; 64(1):136-141.
Luo, X-Y et al., "Detergent interference with Lowry assay of bovine milk fat globule membrane protein," *Biochemical Archives* Nov. 1997; 13(4):319-326.
Mokrasch, L.C. et al., "Purification and Properties of Fructose-1, 6-Diphosphatase," *The Journal of Biological Chemistry* 1956; 221:909-917.
Reisner, A.H. et al., "The use of Coomassie Brilliant Blue G250 perchloric acid solution for staining in electrophoresis and isoelectric focusing on polyacrylamide gels," *Anal. Biochem.* Apr. 1975; 64(2):509-16.
Xu, P-P et al., "Interference by cyclodextrins in protein determination by the Bradford method," *Microchemical Journal* 1994; 49(1):85-90.

\* cited by examiner

*Primary Examiner* — Christopher A Hixson
(74) *Attorney, Agent, or Firm* — Robert W. Prince

(57) ABSTRACT

The invention provides reagents, methods and kits for detection of proteins and quantitative determination of protein concentration. The reagents comprise a protein-complexing dye, such as a Coomassie dye and one or more dextrins, for the elimination of interference caused by detergents.

34 Claims, 3 Drawing Sheets

A

B

B

A

PROTEIN DETECTION REAGENTS AND METHODS WITH DYES AND DEXTRINS

TECHNICAL FIELD

The present invention relates to reagents, methods and kits for detection of proteins and quantitative determination of protein concentration.

BACKGROUND ART

Several methods are available for detecting proteins and determining the concentration of a protein in solution. These include dye-binding methods, which are well known in the art, and involve a non-specific reaction in which a protein-complexing dye binds to the protein. The formation of a dye-protein complex causes a change in the optical properties of the dye, such that there is a colour change proportional to the amount of protein present in the sample. Protein-complexing dyes used for in vitro protein quantitation include bromocresol green (Gindler, U.S. Pat. No. 3,884,637), HABA and methyl orange, but these are of limited use as they bind almost exclusively to albumin and generally are not very sensitive.

Other methods to determine protein concentration include the Biuret method (Mokrasch and McGilvery, J. Biol. Chem. (1956). 221, p. 909), in which peptide structures containing at least two peptide linkages are reacted with $Cu^{2+}$ in alkaline solution to form a violet-coloured chelate complex.

Lowry et al. (J. Lab. Clin. Med. (1951). 39, 663) used a pre-treatment of proteins with an alkaline copper solution, similar to the Biuret method, followed by addition of Folin-Ciocalteu reagent (which contains lithium salts of phosphotungstic and phosphomolybdic acids). The colour produced was a result of the reduction of the phosphotungstic and phosphomolybdic acids to tungsten and molybdenum blue by the Cu-protein complex and by the tryptophan and tyrosine of the protein.

A serious drawback of both the Biuret and Lowry methods is that they cannot tolerate reducing agents that are often present in protein samples.

Dye/protein complex formation using Coomassie Brilliant Blue G-250 as a protein-complexing dye has been described (Bradford U.S. Pat. No. 4,023,933). Coomassie Brilliant Blue dyes will bind to a wide variety of proteins. Moreover, the use of the G-250 dye in the appropriate acid medium results in a protein assay reagent having a sensitivity approximately 100 times greater than the Biuret and conventional dye binding techniques and about 3 to 5 times that of the Lowry method (Bradford U.S. Pat. No. 4,023,933). The use of Coomassie Brilliant Blue G-250 dye in the procedure disclosed in U.S. Pat. No. 4,023,933, the "Bradford Assay", has many advantages over methods that employ other dyes, including high sensitivity, which permits the use of small sample size and utility when reducing agents are present in a sample.

Coomassie Brilliant Blue G-250 exists in two different colour forms, red and blue. The blue form of the dye is present in neutral and alkaline solution while the red form is present in markedly acid solution (pH 0-1). In acidic solution, Coomassie Brilliant Blue G-250 is present in equilibrium between the red and blue forms; such solutions are brownish in appearance. It is believed that as protein binds to the dye, the dye is brought into a different microenvironment and is then protected from the acid medium that gives the red colour to the dye. The strength of the acid medium is important for protein assay sensitivity using Coomassie dyes, because an increase in the strength of the acid medium causes a significant loss in sensitivity of the assay. The protein-dye complex tends to aggregate, which affects the stability of the colour product. The presence of a solubilising agent, such as ethanol, tends to keep the protein-dye complex from aggregating for a reasonable period of time; however, too much ethanol results in a marked shift to the blue form of the dye, i.e., change of the environment to one which is less polar. It has been postulated that the mechanism of the assay is the binding of a carbanion form of the dye to a less polar environment of the protein. This perhaps also explains the negative effect of large quantities of detergent and of acetone on the assay, since these compounds are generally non-polar in nature and would tend to change the environment of the dye.

The principal drawbacks of the Bradford assay are the effective lack of colour stability for extended periods, largely due to precipitation of the protein-dye complex; the failure to show substantially the same reactivity to different proteins; the failure to follow Beer's law; and, most importantly, the adverse affect on the assay of detergents present in a sample (Bradford, M., Anal. Biochem., 72 248-254, 1976 and U.S. Pat. No. 4,023,933).

Dye/protein complex formation is also used for staining proteins in gels, such as those used in electrophoresis. For example, the dye Coomassie Brilliant Blue G-250 in perchloric acid solution has been so used (Reisner, A. H. et al. (1975) Anal. Biochem. 64, 509-516).

Currently, several commercial Coomassie-based formulations are available to stain proteins in gels after electrophoretic separation. For many electrophoretic applications, detergents such as SDS are used to facilitate separation of proteins. Because detergents adversely affect the colour change on binding of Coomassie dyes to protein, the detergent must be removed by several wash procedures, resulting in extended and convoluted staining procedures.

Thus a major disadvantage of dye-based protein detection and quantitation, in particular using Lowry assay reagents or Coomassie dyes, is the interference from detergents, surfactants and other amphipathic molecules.

Accordingly, there is a desire for reagents and methods for detection and quantitative determination of protein which have improved tolerance to the presence of detergents in the samples and which have improved protein-dye colour stability.

DISCLOSURE OF THE INVENTION

The invention provides a reagent for detection of protein comprising, or consisting of:
(a) a protein-complexing dye, and,
(b) one or more dextrins.

The protein-complexing dye is a dye which typically undergoes a change in optical properties on formation of a protein-dye complex, this can be a change in absorption spectra as occurs with Coomassie™ brilliant blue dyes, bromocresol green, HABA, methyl orange, Biuret reagent, Biuret reagent with Folin-Ciocalteu reagent (Lowry reagents); or a change in emission spectra, as occurs for dyes which form a fluorescent protein/dye complex, e.g. Coomassie Orange™, fluorescein, Alexofluor, phycoerythrin, Texas Red™.

It is preferred that the protein-complexing dye does not comprise a protein, preferably the protein-complexing dye does not comprise an antibody or peptide.

The protein-complexing dye is preferably a Coomassie dye, such as a Coomassie brilliant blue dye, e.g. Coomassie brilliant blue dye G-250 or Coomassie brilliant blue dye R-250. For some protein complexing dyes, and in particular Coomassie dyes, a low pH is required to achieve the necessary change in optical properties on protein/dye complex formation.

Accordingly, the invention further provides a reagent for detection of protein comprising:
(a) a protein-complexing dye,
(b) one or more dextrins, and,
(c) an acid with a pKa of 4 or less.

In the reagent, it is preferred that the dye is present at a concentration in the range of from about 0.001% to about 0.1% (w/v), preferably from about 0.005% to 0.05% (w/v). In use the reagent may be diluted, typically the ratio of reagent to diluent, e.g. protein-containing solution, will be in the range of from about 1:1 to about 1:60. For detection of protein in solutions containing 25 µg/ml or less protein, a 1:1 volume ratio of reagent to protein-containing solution could be used. For solutions with a higher protein concentration, e.g. 0.1 mg/ml to 2 mg/ml, a 1:60 volume ratio of reagent to protein-containing solution would be appropriate.

Useful acids have a pKa in the range of 0 to 4, preferably 3 or less so that the reagent has a pH of −1 to 1; more preferably the acid will have a pKa in the range of from about 1 to about 3, so that the reagent has a pH of 0 to 1. Many useful acids are identified in the Bradford patent (U.S. Pat. No. 4,023,933) and Gindler patent (U.S. Pat. No. 4,239,495), suitable acids include a phosphoric acid, a phosphorous (phosphonic) acid, periodic acid, selenic acid, maleic acid, oxalic acid and dichloroacetic acid. Phosphoric and phosphonic acids are preferred. A preferred phosphonic acid is Nitrilotris (methylene) triphosphonic acid (NTP), a commercially available polybasic acid.

In a reagent according to the invention, when acid is present, it will generally be present at a concentration of from about 4% to about 20% preferably from about 4% to about 12%, preferably from about 7.5% to about 9.5% (w/v). The reagent may be diluted in use such that the final concentration of acid will be in the range of from about 2% to about 20%.

The acid can be a mixture of polybasic and monobasic acid, in such mixtures it is preferred that the ratio of polybasic to monobasic acid is in the range of from about 2:1 to about 3:1. In the reagent, a polybasic/monobasic acid mixture is generally present at a concentration in the range of from about 1 to about 15% (v/v), preferably of from about 2% to about 5% (v/v). For use, the reagent may be diluted to give a final concentration of the polybasic/monobasic acid mixture in the range of from about 0.5 to about 15%.

A reagent according to the invention comprises one or more dextrins, preferably selected from a linear dextrin (D), a cyclodextrin (CD), a cycloamylose (CA) and derivatives thereof. A preferred reagent comprises one or more cyclodextrins. Suitable linear dextrins comprise 6 or more glucose units, preferably 10 or more glucose units, e.g. 15 glucose units; cyclodextrins will generally have 6 (α-CD), 7 (β-CD), or 8 (γ-CD) glucose units; cycloamyloses will generally comprise 8 or more glucose units. Suitable derivatives include heptakis 2,6-di-o-butyl β-cyclodextrin, carboxymethyl β-cyclodextrin and carboxymethyl α-cyclodextrin.

Mixtures of dextrins may be used, for example mixtures of cyclic dextrins, such as two or more cyclic dextrins selected from α-CD, β-CD and γ-CD; two or more cyclic dextrins selected from α-CD, β-CD, γ-CD and CA; mixtures of linear and cyclic dextrins such a linear dextrin and one or more of α-CD, β-CD and γ-CD; or a linear dextrin and one or more of α-CD, β-CD, γ-CD and CA. Unless the context directs otherwise, the term "dextrin" as used herein encompasses dextrins and dextrin derivatives.

Some derivatives of cyclodextrin, dextrin and certain cycloamyloses may act as surfactants and may be less suited for use in reagents, methods and kits of the invention. Some dextrins at certain concentrations will interfere with the certain dyes due to the surface-active properties of the dextrin. The dextrins and their respective interfering concentrations for different dyes can be easily determined by those skilled in the art.

For a given protein, the choice of dextrin or mixture of dextrins used may be optimised and where one or more dextrin is used, the ratio may be adjusted to achieve the most effective conditions for detection and/or quantification of a given protein or protein sample.

In reagents of the invention the dextrin(s) will generally be present at a concentration in the range of from 0.01 to 200 mg/ml, preferably in the range of from 0.5 to 50 mg/ml. Where mixtures of dextrins are used these concentrations relate to the total dextrin concentration. Dilution of the reagent may be adjusted such that the final concentration of dextrin is optimised for a given protein and protein concentration. When a detergent is present in the protein sample, the choice and concentration of dextrin(s) may be optimised for a given detergent and a particular concentration of the detergent. Appropriate final dextrin concentrations can be easily determined by those skilled in the art for example by measuring absorbance or emission spectra, as appropriate, of the protein-dye complex in the presence of various concentrations of the dextrin or mixture of dextrins. For Coomassie brilliant blue G-250, absorption can be measured at the absorption peak, 595 nm.

A reagent according to the invention may further comprise a solubilising agent, such as an alcohol, to maintain solubility of the dye-protein complex. The solubilising agent can be any agent that reduces or delays precipitation of the dye-protein complex.

One or more alcohols may be included in the reagent, suitable alcohols include ethanol, methanol and propanol. Other appropriate alcohols are those with good water solubility that show little or no behaviour as detergents. When alcohol is present in the reagent, the concentration is generally from 0.1% to about 10% (v/v), preferably from about 0.1% to about 5% (v/v), more preferably from about 1% to about 5% (v/v).

A reagent of the invention may comprise a detergent.

The reagent can be provided in a multipart system, e.g. as one or more aqueous components, which are combined to form a reagent of the invention. If provided in two parts, one part may comprise the dye, optionally acid and/or optionally alcohol, whilst the other may comprise the dextrin(s). Each individual component has extended stability (for about one year when kept refrigerated) and when mixed to form the reagent, the reagent itself is stable for more than 6 months when kept refrigerated at 4° C. A reagent according to the invention may be generated by combining one or more dextrin(s) with commercially available protein staining reagents, e.g. Bradford assay reagents or other Coomassie protein staining reagents. Commercially available protein staining reagents, methods and kits; in particular commercially available Bradford assay reagents methods and kits, can be adapted by inclusion of one or more dextrins in accordance with the invention. Examples of such commercially available kits include the following:

Pierce:
23236 Coomassie Plus—The Better Bradford Assay Kit (includes standards)
23238 Coomassie Plus—The Better Bradford Assay Reagent
23200 Coomassie (Bradford) Protein Assay Kit 23296 Coomassie (Bradford) Dry Protein Assay Plates 2×96 well
23596 Coomassie (Bradford) Dry Protein Assay Plates 5×96 well
BioRad:
500-0201EDU Quick Start Bradford Protein Assay Kit 1
500-0202EDU Quick Start Bradford Protein Assay Kit 2
500-0203EDU Quick Start Bradford Protein Assay Kit 3
500-0204EDU Quick Start Bradford Protein Assay Kit 4
500-0006EDU Bio-Rad Protein Assay Dye Reagent Concentrate
Sigma Aldrich:
B6916 Bradford Reagent (Sigma)
27813 Coomassie® protein assay reagent BioChemika (Fluka)

Conventionally, detection and quantitation of protein using some protein-complexing dyes is subject to very significant interference from detergents; particularly adversely affected are the protein complexing dyes Coomassie blue G-250, Coomassie Red G-250, Coomassie Orange, Biuret reagent and Biuret reagent with Folin-Ciocalteu reagent. This invention overcomes these difficulties. Without wishing to be bound by theory, it is believed that the detergent forms a complex with the dextrin and the affinity of the detergent for the dextrin is higher than the affinity of the detergent for the dye. By using a suitable amount of a dextrin or a mixture of dextrins, the detergent can be trapped in a dextrin-detergent complex, thereby, limiting the degree to which the detergent inhibits the protein-dye reaction.

Compared to currently available reagents for protein detection, reagents of the invention can be used successfully when detergents are present in the protein-containing samples. This is of great significance as reagents of the invention allow protein detection in an environment rich in detergents or surfactants, such as may be required to solubilize membrane proteins or to extract proteins directly from micro-organisms using detergent rich solutions, e.g. commercially available extraction solutions such as B-PER®, and CelLytic™.

The invention further provides a method of detecting protein comprising contacting a protein-containing sample with a solution comprising:
(a) a protein-complexing dye, and,
(b) one or more dextrins,
and detecting formation of a dye/protein complex.

For dyes that require strongly acidic conditions, the invention provides a method of detecting protein comprising contacting a protein-containing sample with a solution comprising:
(a) a protein-complexing dye,
(b) one or more dextrins, and,
(c) an acid with a pKa of 4 or less;
and detecting formation of a dye/protein complex.

Detecting the formation of dye/protein complex may comprise quantifying the amount of dye/protein complex formed, so as to determine the concentration of protein in the sample.

In a further embodiment the invention provides a method of quantifying protein comprising contacting a sample containing protein with a solution comprising:
(a) a protein-complexing dye,
(b) one or more dextrin(s),
and quantifying dye/protein complex formation.

For dyes that require a strongly acidic environment, the invention provides a method of quantifying protein comprising contacting a sample containing protein with a solution comprising:
(a) a protein-complexing dye,
(b) one or more dextrin(s), and,
(c) an acid with a pKa of 4 or less;
and quantifying dye/protein complex formation.

The protein-containing sample can be a solution, or the protein-containing sample can be provided on a support, such as a gel, sol, chromatography plate, filter paper, nitrocellulose membrane or resin.

Accordingly, in an additional embodiment the invention further provides a method of detecting protein comprising:
(a) providing a support comprising protein,
(b) contacting the protein with a solution comprising:
(i) a protein-complexing dye, and,
(ii) one or more dextrin(s),
and detecting dye/protein complex formation.

For protein complexing dyes that require acidic conditions, the invention provides a method of detecting protein comprising:
(a) providing a support comprising protein,
(b) contacting the protein with a solution comprising:
(i) a protein-complexing dye,
(ii) one or more dextrin(s), and,
(iii) an acid with a pKa of 4 or less;
and detecting dye/protein complex formation.

Suitable protein complexing dyes, dextrins and, if required, acids for inclusion in the solution used in methods of the invention are described above. The protein-complexing dye, one or more dextrin(s) and, if present, acid with a pKa of 4 or less, can be provided by a reagent according to the invention, which may be diluted to form the solution. The solution may comprise a solubilising agent such as an alcohol as described herein.

The support can be a gel, sol, chromatography plate, filter paper, nitrocellulose membrane or resin. The support may comprise a detergent. Using methods of the invention contacting can be performed in the presence of a detergent. These methods are particularly suitable for detecting protein in polyacrylamide gel, agarose gel or polymer composite gel, for example when a protein sample has been separated using an electric field, e.g. by electrophoresis.

The reagents and methods described herein for the detection and quantitative determination of protein in gels, such as those produced following separation using an electric field, e.g. by electrophoresis, simplify conventional procedures so that washing procedures to remove detergents such as SDS and excessive stain (background stain) are no longer required.

Typically, the methods are carried out at room temperature.

In methods of the invention detecting formation of a dye protein complex may comprise detecting a change in absorption or emission spectra of the dye/protein complex. In some instances, a colour change may be detected; for example when using Coomassie brilliant blue dyes such as G-250. Colour changes may be detected using conventional apparatus, such as a colorimeter, for example capable of measuring absorbance at a wavelength in the range of from 570 nm to 620 nm.

For dyes that undergo a change in absorption spectra on formation of a protein/dye complex, detecting can be performed by measuring absorbance, for example using a spectrophotometric method. Conventional apparatus may be used for spectrophotometric analyses, such as a UV/VIS Spectrophotometer with a wavelength range of from 400 to 700 nm.

For dyes that undergo a change in emission spectra on formation of a protein/dye complex, detecting can be performed by measuring emission, for example using a spectrofluorimeter (luminescent spectrometer), suitably with a wavelength range of 190 nm to 800 nm.

Detecting the protein/dye complex may comprise quantifying the amount of protein/dye complex present so as to determine the amount or concentration of protein. Quantifying can be performed by methods that comprise measuring a change in absorption or emission spectra of the dye/protein complex. Quantifying may comprise for example measuring a colour change. As described absorbance can be measured by a spectrophotometric method and change in absorbance over time may be measured. Absorbance is generally measured at a wavelength in the range of from about 400 to about 700 nm.

For Coomassie brilliant blue G-250, absorbance is measured at a wavelength of about 595 nm, the absorbance maximum for this dye when complexed to protein. When using Coomassie brilliant blue G-250, protein can be detected by monitoring of the increase in absorbance at 595 nm due to formation of the dye/protein complex.

To determine protein concentration, the absorbance or emission measured can be compared with a standard value, standard set of values, or standard curve. The results are highly reproducible and accurate as shown in the Examples.

Because of the high sensitivity displayed using reagents and methods of the invention, protein concentrations can be selected which are as low as approximately 0.1 µg per 1 ml of sample. Moreover, the time required for such accurate and sensitive determinations is less than about 2 minutes per sample in contrast to 30-40 minutes generally required for traditional Lowry or Biuret type assays. Consequently, methods of this invention are highly amenable to automation and analysis of large numbers of samples.

The invention further provides kits for detecting and/or quantifying protein, the kits comprising one or more dextrin(s). Kits for detecting and/or quantifying protein may comprise one or more dextrins and a protein-complexing dye. Additionally, a kit may comprise one or more acid(s) and/or alcohol(s) as described herein. A kit for detecting and/or quantifying proteins in accordance with the invention may comprise a reagent of the invention, which may be provided as a multipart system wherein the components are mixed to form a reagent of the invention.

The invention further provides the use of one or more dextrin(s) to enhance formation of a protein-binding dye/protein complex in the presence of a detergent.

Furthermore, the invention provides the use of one or more dextrins to reduce interference of a detergent in formation of a protein-binding dye/protein complex in the presence of a detergent.

The invention yet further provides the use of one or more dextrins to alter the optical properties of a dye, such as a protein-complexing dye, in the presence of a detergent.

Both methods give reasonable linear response for samples free of detergent. The slope of the curve and the correlation coefficient are comparable for both methods indicating the dextrins included in the reagent do not interfere with protein-dye binding.

Figure 1:
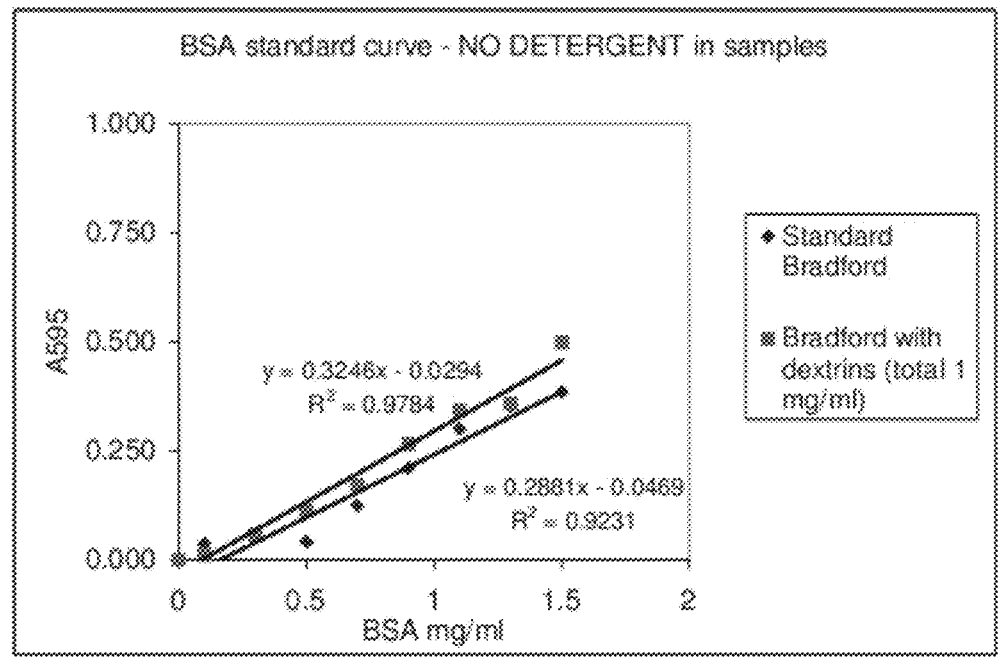
FIG. 1: Standard curves for protein samples without detergent
Figure 1:
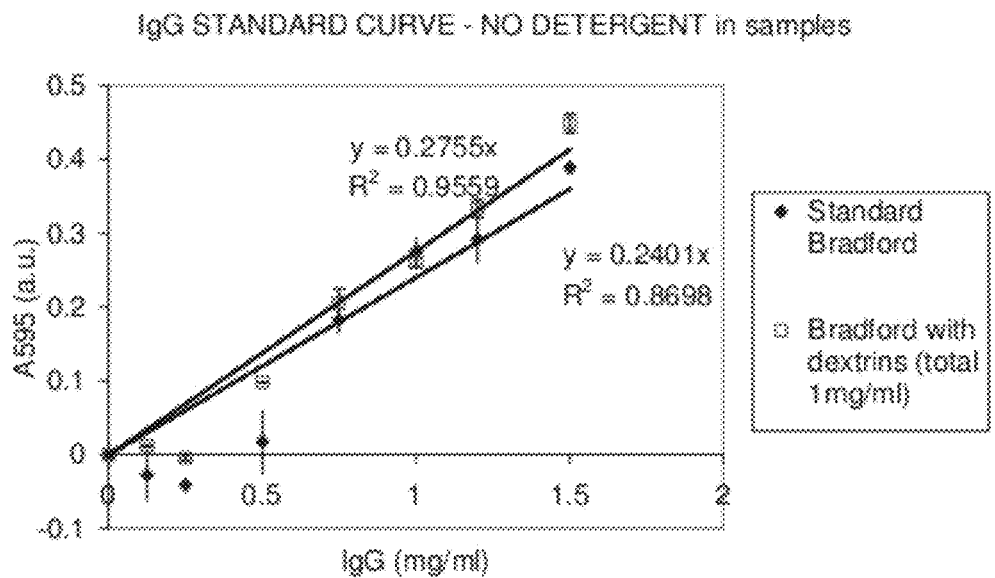
Figure 2:
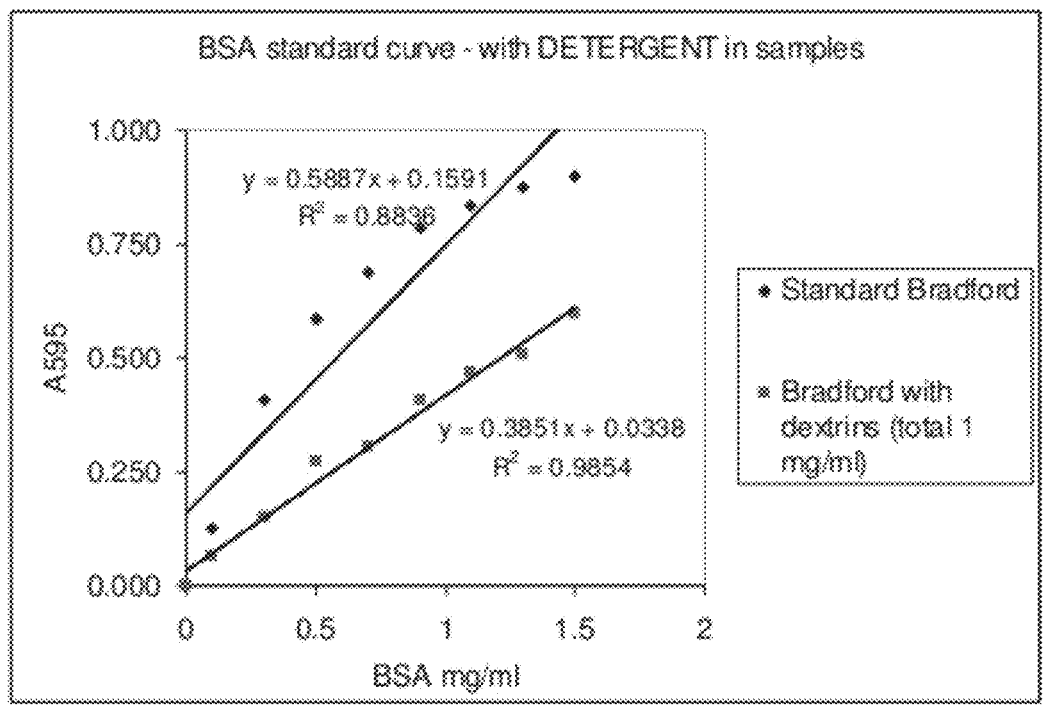
Figure 2:
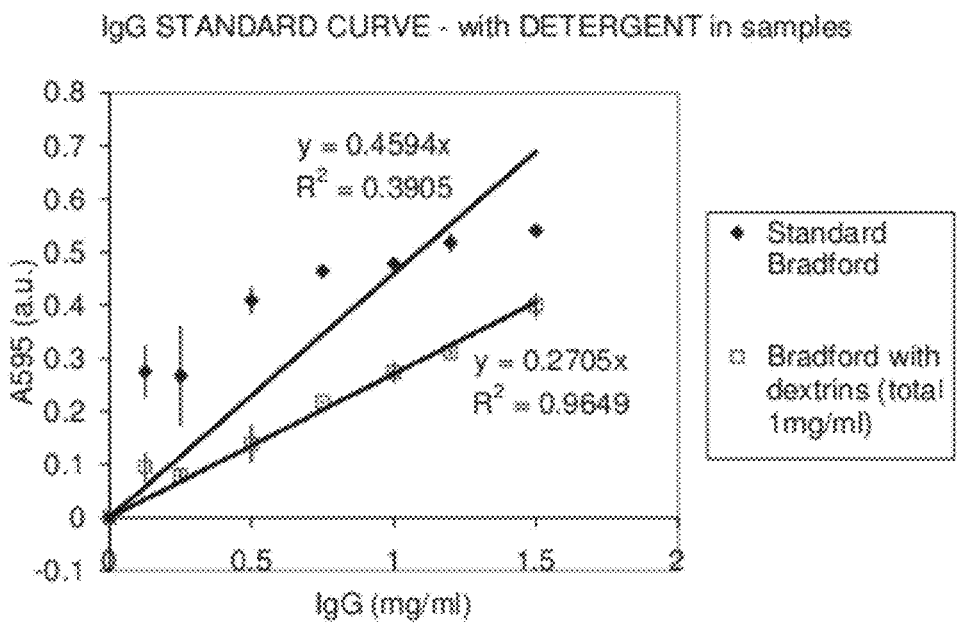

FIG. 2: Standard curves for protein samples including detergent (0.25% CTAB). Only the reagent including dextrins gives a linear response with the slopes and the correlation coefficient being comparable to the slopes and correlation coefficient for samples without detergent.

Figure 3:
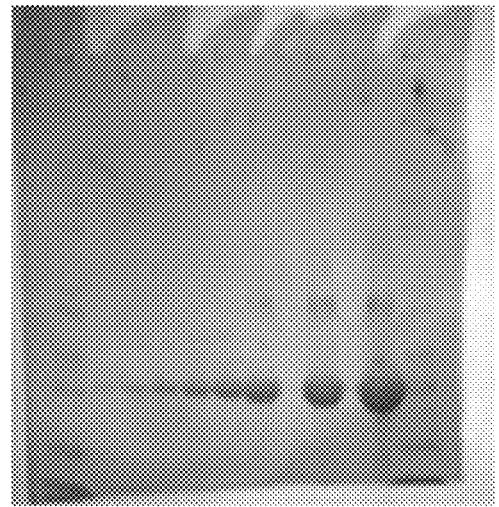
Figure 3:
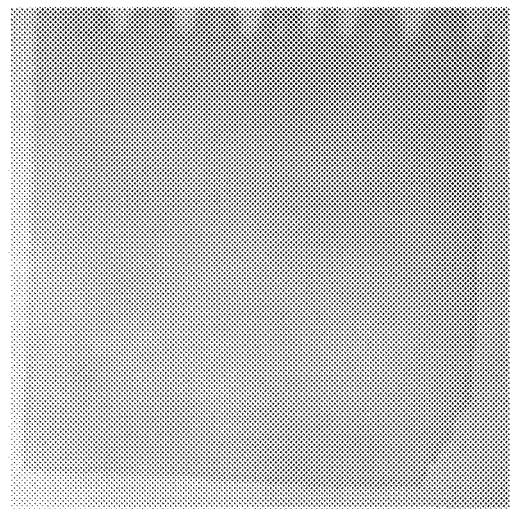

FIG. 3: Detection of protein in polyacrylamide gel
The following samples were run on each gel:
Lane 1 Molecular weight standard, Mark 12™
Lane 2 Beta-lactoglobulin 0.08 mg/ml
Lane 3 Beta-lactoglobulin 0.16 mg/ml
Lane 4 Beta-lactoglobulin 0.31 mg/ml
Lane 5 Beta-lactoglobulin 0.63 mg/ml
Lane 6 Beta-lactoglobulin 1.25 mg/ml
Lane 7 Beta-lactoglobulin 2.5 mg/ml
Lane 8 Empty
Lane 9 Beta-lactoglobulin 5 mg/ml
Lane 10 Empty
Lane 11 Beta-lactoglobulin 10 mg/ml
Lane 12 Molecular weight standard Gel B was stained with solution B, gel A was stained with solution A, as described in Example 3. The gels were photographed after 1 hour 45 minutes incubation in the staining solutions.

EXAMPLES

Example 1

Preparation of Bradford Reagent

To 100 mg Coomassie Brilliant Blue (G-250) was added 47 g ethanol, 85 g phosphoric acid and 850 g water. This solution was mixed for 20 minutes, to ensure all components were dissolved, resulting in a reagent comprising 0.01% (w/v) Coomassie Brilliant Blue G-250, 4.7% ethanol (w/v) and 8.5% (w/v) phosphoric acid. To this solution different dextrins were added as indicated in the specific examples.

Bradford Assay (Standard Method)

Five microliters of sample solutions containing from 0.1 mg/ml to 1.5 mg/ml protein and/or from 0.00% to 0.5% detergent were pipetted into the wells of 96-well microtitre plates. To this was added 300 microliters of Bradford reagent. The absorbance was measured at 595 nm.

Reducing Detergent Interference

Five different detergents were used in the experiment, namely sodium dodecylsulphate (SDS) (anionic), Cetyltrimethylammonium bromide (CTAB) (cationic), TWEEN™-20 (non-ionic), TRITON™-X 100 (non-ionic) and Brij-35 (non-ionic). Four different dextrins were used in the experiment, namely dextrin-15 (D15), alpha-cyclodextrin (α-CD), beta-cyclodextrin (β-CD) and gamma-cyclodextrin (γ-CD), an equimass mixture of these dextrins (MIX) was also used. In addition, different cycloamylose concentrations were also tested.

A) Bradford assay containing a total of 100 mg/ml dextrin(s) or saturated concentration of the various dextrin(s).

| Table of absorbance measured at 595 nm blanked against a water sample. | | | | | | |
|---|---|---|---|---|---|---|
| | No dextrin | D15 | α-CD | β-CD | γ-CD | MIX |
| SDS (0.5% w/v) | 0.326 | 0.007 | 0.013 | 0.089 | 0.038 | 0.047 |
| CTAB (0.25% w/v) | 0.785 | 0.024 | 0.003 | 0.067 | 0.015 | 0.020 |
| TWEEN-20 (0.25% w/v) | 1.027 | 0.453 | 0.134 | 0.077 | 0.344 | 0.041 |
| TRITON-X 100 (0.10% w/v) | 0.677 | 0.101 | 0.034 | 0.017 | 0.022 | 0.003 |
| Brij-35 (0.50% w/v) | 0.231 | 0.035 | 0.015 | 0.019 | 0.143 | 0.018 |

B) Bradford assay containing a total of 10 mg/ml dextrin(s) of the various dextrin(s).

Table of absorbance measured at 595 nm blanked against a water sample.

|  | No dextrin | D15 | α-CD | β-CD | γ-CD | MIX |
|---|---|---|---|---|---|---|
| SDS (0.5% w/v) | 0.326 | 0.051 | 0.003 | 0.025 | 0.005 | 0.000 |
| CTAB (0.25% w/v) | 0.785 | 0.184 | 0.026 | 0.029 | 0.164 | 0.008 |
| TWEEN-20 (0.25% w/v) | 1.027 | 0.855 | 0.167 | 0.171 | 0.625 | 0.376 |
| TRITON-X 100 (0.10% w/v) | 0.677 | 0.076 | 0.003 | 0.006 | 0.019 | 0.095 |
| Brij-35 (0.50% w/v) | 0.231 | 0.046 | −0.02 | 0.001 | 0.007 | 0.026 |

C) Bradford assay containing a total of 1 mg/ml dextrin(s) of the various dextrin(s).

Table of absorbance measured at 595 nm blanked against a water sample.

|  | No dextrin | D15 | α-CD | β-CD | γ-CD | MIX |
|---|---|---|---|---|---|---|
| SDS (0.5% w/v) | 0.326 | 0.195 | 0.010 | 0.056 | 0.079 | 0.020 |
| CTAB (0.25% w/v) | 0.785 | 0.674 | 0.163 | 0.176 | 0.603 | 0.407 |
| TWEEN-20 (0.25% w/v) | 1.027 | 0.999 | 0.842 | 0.803 | 0.952 | 0.947 |
| TRITON-X100 (0.10% w/v) | 0.677 | 0.248 | 0.288 | 0.040 | 0.032 | 0.003 |
| Brij-35 (0.50% w/v) | 0.231 | 0.098 | 0.003 | 0.033 | 0.040 | 0.002 |

D) Bradford assay containing various concentrations of cycloamylose (CA).

Table of absorbance measured at 595 nm blanked against a water sample.

|  | No dextrin | CA 10 mg/ml | CA 1 mg/ml |
|---|---|---|---|
| SDS (0.1% w/v) | −0.063 | −0.072 | −0.023 |
| CTAB (0.1% w/v) | 0.412 | −0.081 | 0.003 |
| TWEEN-20 (0.1% w/v) | 0.462 | 0.074 | 0.352 |
| TRITON-X 100 (0.1% w/v) | 0.677 | −0.024 | 0.410 |
| Brij-35 (0.1% w/v) | −0.024 | −0.025 | −0.011 |

The absorbance at 595 nm provides an indication of the amount of the blue form of the Coomassie G-250 dye. At a given concentration of a particular detergent, a high absorbance value indicates high background, due to the presence of the detergent, such that that the blue colour detected is not representative of the amount of protein-dye complex present and thus is not representative of the protein concentration. It can be seen that for each of the detergents tested, the presence of a dextrin or dextrins in the solution resulted in a lower absorbance value, indicating that there is less background interference and that the presence of dextrin increases the sensitivity and accuracy of protein detection. For a given detergent the optimal choice of dextrin and concentration of dextrin can be determined by measuring absorbance at the absorbance peak of the dye/protein complex in the presence of various concentrations of dextrins and combinations thereof.

Example 2

Linearity of Standard Curves in Presence of Detergents

A dilution series of two different proteins, bovine serum albumin (BSA) (Pierce, 23209) and bovine immunoglobulin (IgG) (Sigma, I5506) was created in the concentration range 0.1 mg/ml to 1.5 mg/ml. CTAB was chosen as detergent and was added to the protein samples to a concentration of 0.25% (w/v). Bradford assays were performed with Bradford reagent containing 0.25 mg/ml dextrin-15 (D15), 0.25 mg/ml alpha-cyclodextrin (α-CD), 0.25 mg/ml beta-cyclodextrin (β-CD) and 0.25 mg/ml gamma-cyclodextrin (γ-CD), these were compared with Bradford assay performed with Bradford reagent containing no dextrins.

Example 3

Detection of Protein in Polyacrylamide Gel

Preparation of Gel Staining Solutions

To 80 mg Coomassie Brilliant Blue (G-250) was added 50 g ethanol, 80 g phosphoric acid and 850 g water. The solution was mixed for 20 minutes to ensure all components were dissolved—this was solution A. Following this, solution B was made by adding 250 mg dextrin-15, 250 mg alpha-cyclodextrin (α-CD), 250 mg beta-cyclodextrin (β-CD) and 250 mg gamma-cyclodextrin (γ-CD) to 100 ml of solution A.

Preparation of the Samples and Gels

A dilution series of beta-lactoglobulin (BLG) (Sigma, L-0130) was prepared in the concentration range 0.08 mg/ml to 10 mg/ml. Thirty microliters of the sample was diluted with ten microliters Nupage LDS Sample buffer (Invitrogen, NP0007). Duplicate gels were prepared, fifteen microliters of each sample was loaded onto each gel (Nupage 10% Bis-Tris, Invitrogen, NP0302). Ten microliters of the Mark 12™ molecular weight standard (Invitrogen, LC5677) was also loaded in the gel. The gels were run at constant voltage (200V) for 35 min in standard MES buffer. Following this, one gel was submerged in 25 ml of solution B (a staining solution which consisted of 25 ml of solution A as described above containing a mixture of dextrins as follows: 2.5 mg/ml dextrin-15 (D15), 2.5 mg/ml alpha-cyclodextrin (α-CD), 2.5 mg/ml beta-cyclodextrin (β-CD) and 2.5 mg/ml gamma-cyclodextrin (γ-CD)). The other gel was submerged in a staining solution consisting of 25 ml of solution A. After 1 hour 45 minutes incubation in the staining solutions, the gels were photographed (FIG. 3).

The invention claimed is:

1. A method of detecting and/or quantifying protein comprising contacting a protein-containing sample with a solution comprising:
   (a) a protein complexing dye; and
   (b) one dextrin selected from α-cyclodextrins, γ-cyclodextrins, linear dextrins and derivatives thereof, or two or more dextrins; and
detecting and/or quantifying dye/protein complex formation, wherein the protein is in the presence of a detergent.

2. The method according to claim 1, wherein the protein is in solution or the protein is provided on a support.

3. The method according to claim 2, wherein the support is a gel, sol, chromatography plate, filter paper, nitrocellulose membrane or resin.

4. The method according to claim 3, wherein the support is a polyacrylamide gel or agarose gel and the protein has been subjected to separation using an electric field.

5. The method according to claim 2, wherein the support comprises a detergent and/or wherein contacting is performed in the presence of a detergent.

6. The method according to claim 1, wherein detecting and/or quantifying comprises detecting a change in absorption or emission spectra of the dye/protein complex.

7. The method according to claim 6, wherein detecting and/or quantifying comprises detecting a colour change.

8. The method according to claim 6, wherein the protein-complexing dye is a Coomassie G-250 dye and absorbance is measured at a wavelength of about 595 nm.

9. The method according to claim 1, wherein quantifying is performed by measuring absorbance over time.

10. The method according to claim 6, wherein the absorbance or emission measured is compared with a standard value, standard set of values, or standard curve.

11. The method according to claim 1, further comprising providing a support comprising protein, prior to the contacting step.

12. A method comprising contacting a protein-containing sample in the presence of a detergent with a protein binding dye, and one dextrin selected from α-cyclodextrins, γ-cyclodextrins, linear dextrins and derivatives thereof; and detecting and/or quantifying dye/protein complex formation, wherein the protein is in the presence of a detergent.

13. A method of detecting and/or quantifying protein comprising contacting a protein-containing sample in the presence of a detergent with a protein binding dye, and two or more dextrins; and detecting and/or quantifying dye/protein complex.

14. The method according to claim 1, wherein the one dextrin or two or more dextrins are provided as a reagent comprising a protein-complexing dye and one dextrin.

15. The method according to claim 14, wherein the reagent is a reagent concentrate.

16. The method according to claim 14, wherein the reagent further comprises an acid with a pKa of 4 or less.

17. The method according to claim 14, wherein the reagent further comprises a solubilizing agent.

18. The method according to claim 14, wherein the reagent does not comprise a protein.

19. The method according to claim 14, wherein the dye is a Coomassie dye.

20. The method according to claim 1, wherein the one dextrin, or two or more dextrins concentration is in the range of from about 0.01 to about 200 mg/ml.

21. The method according to claim 14, wherein the reagent further comprises one or more alcohols, and wherein the alcohol concentration is from about 0.1% to about 10% v/v.

22. The method according to claim 13, wherein the mixture of two or more dextrins is selected from the group consisting of α-cyclodextrins, β-cyclodextrins, γ-cyclodextrins, cycloamylose, linear dextrins and derivatives thereof.

23. The method according to claim 14, wherein the reagent is provided as a multipart system.

24. A method of detecting and/or quantifying protein comprising contacting a protein-containing sample with a solution comprising:
   (a) a protein-complexing dye, wherein the dye is a Coomassie dye; and
   two or more dextrins; and
detecting and/or quantifying dye/protein complex formation, wherein the protein is on a support.

25. A method according to claim 24, wherein the dye is a Coomassie dye.

26. A method according to claim 24, wherein the support is a gel, sol, chromatography plate, filter paper, nitrocellulose membrane or resin.

27. The method according to claim 26, wherein the support is a polyacrylamide gel or agarose gel and the protein has been subjected to separation using an electric field.

28. The method according to claim 24, wherein the support comprises a detergent and/or wherein contacting is performed in the presence of a detergent.

29. A method of detecting and/or quantifying protein comprising contacting a protein-containing sample with a solution comprising:
   (a) a protein-complexing dye; and
   (b) one dextrin selected from α-cyclodextrins, γ-cyclodextrins, linear dextrins and derivatives thereof; and
detecting and/or quantifying dye/protein complex formation, wherein the protein is on a support.

30. A method according to claim 29, wherein the dye is a Coomassie dye.

31. The method according to claim 30, wherein the Coomassie dye is a Coomassie G-250 dye.

32. A method according to claim 29, wherein the support is a gel, sol, chromatography plate, filter paper, nitrocellulose membrane or resin.

33. The method according to claim 32, wherein the support is a polyacrylamide gel or agarose gel and the protein has been subjected to separation using an electric field.

34. The method according to claim 29, wherein the support comprises a detergent and/or wherein contacting is performed in the presence of a detergent.

\* \* \* \* \*